United States Patent
Wada et al.

[11] Patent Number: 5,994,614
[45] Date of Patent: Nov. 30, 1999

[54] ABSORBENT ARTICLE

[75] Inventors: Ichiro Wada; Chimari Fujita, both of Ehime, Japan

[73] Assignee: Uni-Charm Corporation, Ehime, Japan

[21] Appl. No.: 08/923,262

[22] Filed: Sep. 4, 1997

[30]     Foreign Application Priority Data

Sep. 12, 1996  [JP]  Japan .................................. 8-242066
Mar. 28, 1997  [JP]  Japan .................................. 9-077447

[51] Int. Cl.⁶ .................................................. A61F 13/15
[52] U.S. Cl. ...................................... 604/378; 604/385.1
[58] Field of Search .................................. 604/378–380, 604/385.1, 368

[56]            References Cited

U.S. PATENT DOCUMENTS

| | | | |
|---|---|---|---|
| 4,251,643 | 2/1981 | Harada et al. | 604/368 |
| 4,578,070 | 3/1986 | Holtman | 604/385.1 |
| 4,842,594 | 6/1989 | Ness | 604/378 |
| 5,037,409 | 8/1991 | Chen et al. | 604/378 |
| 5,423,786 | 6/1995 | Fung et al. | 604/379 |
| 5,458,592 | 10/1995 | Abuto et al. . | |
| 5,505,719 | 4/1996 | Cohen et al. | 604/378 |
| 5,506,035 | 4/1996 | Van Phan et al. . | |
| 5,516,569 | 5/1996 | Veith et al. . | |
| 5,652,041 | 7/1997 | Buerger et al. . | |

FOREIGN PATENT DOCUMENTS

| | | |
|---|---|---|
| 0158914 | 10/1985 | European Pat. Off. . |
| 0297411 | 1/1989 | European Pat. Off. . |
| 0539703 | 5/1993 | European Pat. Off. . |
| 2119193 | 8/1972 | France . |
| 2654752 | 5/1991 | France . |
| 3508280 | 9/1986 | Germany . |
| 8815855 | 4/1989 | Germany . |
| S61-30041 | 7/1986 | Japan . |
| S63-23078 U | 6/1988 | Japan . |
| H6-254118 | 9/1994 | Japan . |
| H7-73591 | 8/1995 | Japan . |
| 2189705 | 11/1987 | United Kingdom . |
| WO89/10084 | 11/1989 | WIPO . |
| WO92/14430 | 9/1992 | WIPO . |
| WO95/21596 | 8/1995 | WIPO . |
| WO95/24878 | 9/1995 | WIPO . |
| WO96/06590 | 3/1996 | WIPO . |

*Primary Examiner*—John G. Weiss
*Assistant Examiner*—Dennis Ruhl
*Attorney, Agent, or Firm*—Koda & Androlia

[57]            ABSTRACT

After overlaying an inner sheet of a coarse and bulky non-woven fabric on an outer sheet, super absorbent polymers (SAP) are dispersed on the inner sheet. Folding inwardly both the sides of the laminated body composed of the outer sheet and the inner sheet so as to face the inner sheet together to overlay both the ends together, the SAP are wrapped by means of the outer sheet and the inner sheet from the top and bottom thereof. Then, applying heat over the outer sheet, the outer sheet and the inner sheet are melted and bonded together while the inner sheet is melted and bonded together. Then, the bonding parts are formed in a given shape and SAP can be retained between the fibers of the inner sheet in a given area of the encircled region preliminarily encircled by the bonding parts.

20 Claims, 4 Drawing Sheets

ABSORBENT ARTICLE

BACKGROUND OF THE INVENTION

1. Field of the Invention

The present invention relates to an absorbent article for use in disposable diapers, protectors against incontinence or sanitary napkins; more specifically, the present invention relates to a super absorbent article of a slim type.

2. Prior Art

In disposable diapers and sanitary napkins, an absorption core to absorb urine and blood of menstruation is interposed between the back sheet comprising a liquid non-permeable resin sheet and an inner top sheet in direct contact to the skin of a wearer. Between the upper sheet and lower sheet comprising thin papers in the absorbent core is interposed a mixture of ground pulp and super absorbent polymers (abbreviated as "SAP" hereinafter) such as polyacrylic acid salts or is interposed SAP singly. Because SAP have higher absorptivity than that of pulp, such absorption core interposed with SAP exerts more excellent absorptivity of urine and blood of menstruation, compared with an absorption core interposed only with pulp, so that the resulting absorption core can be prepared of a slim type. Additionally, SAP are powdery at its dry state; once SAP absorb urine and blood of menstruation, however, SAP swell and is then solidified in the form of gel. Therefore, absorbed urine or blood of menstruation can be retained securely in the absorption core, which can prevent the reversion or outward oozing of the absorbed urine and blood of menstruation. Additionally because SAP are softer even at its dry state and swelling state (in the form of gel) than pulp, the absorption core using SAP are so softer than an absorption core using only pulp that the absorption core can readily deform along the body of a wearer, which presents comfortable feeling on wearing.

When the amount of SAP is increased in the absorption core so as to elevate the absorptivity, the SAP powder at its dry state prior to absorption shifts in the absorption core following the motion of a wearer, with the resulting variation in the SAP distribution. When urine or blood of menstruation is spotted at a part with a lower content of SAP, then, the urine or blood of menstruation cannot be absorbed into the smaller amount of SAP, with the resulting deterioration of the absorptivity. After absorption, furthermore, the SAP gel may shift to be solidified in the absorption core or the resulting mass might tear or break the upper sheet and lower sheet, disadvantageously, which presents unpleasant feeling to a wearer.

So as to overcome the problems described above, for example, Japanese Patent Publication No.61-30041, Japanese Patent Provisional No. 6-254118, and Japanese Patent Publication No.7-73591 and furthermore Japanese Utility Model Publication No.63-23078 describe an invention or a utility model, relating to an absorption core produced by dispersing a given amount of a super absorbent material at an interval on the whole surface of a sheet, covering a cover sheet with a great number of recesses formed thereon over the sheet, and bonding the cover sheet to the sheet.

In such manner, the super absorbent material is pressed against a part to be placed, by uniformly distributing a given amount of a super absorbent material over the whole absorption core and covering such cover sheet over the absorption core. Hence, the shift of the super absorbent material in the absorption core can be prevented, while the whole thickness of the absorption core can be uniformly retained and the absorptivity can be enhanced.

In the absorption core as described above, the depth and diameter of each of the recesses on the cover sheet should be sufficiently enlarged so as not to prevent the swelling of the super absorbent material, so that the volume of the space inside each of the recesses should be larger than the volume of the given amount of the super absorbent material. Therefore, the dimension of the thickness of the absorption core is so large, which limits the preparation of an absorbent article of a slim type. When the space in each of the recesses on the cover sheet is made small so as to prepare an absorption core of a slim type, the swelling of the super absorbent material is prevented when the core absorbs urine or blood of menstruation, which reduces the absorptivity.

Furthermore, when covering a cover sheet over the absorption core, the cover sheet should cover a sheet mounting the super absorbent material, so that the super absorbent material is to be placed just in the recesses formed on the cover sheet. Then, the cover sheet should be bonded to the sheet mounting the super absorbent material at a part between individual recesses on the cover sheet. Accordingly, the bonding lines on which the cover sheet is bonded to the sheet mounting the super absorbent material are so complex that the bonding work of both the sheets is laborious.

The present invention can overcome the aforementioned problems of prior art and provides an absorbent article capable of preventing the shift of the absorbent material in the absorption core and dispersing uniformly the absorbent material over the whole absorption core without exception and secururing a zone where the absorption material after absorption can swell.

It is another object of the present invention to provide an absorbent article of a slim type, which can absolutely prevent the outward pouring of the absorbent material and can be produced readily.

SUMMARY OF THE INVENTION

The absorption core to be used in accordance with the present invention comprises a plurality of outer sheets (simply referred to as "outer sheet" hereinbelow) at a higher density, a bulky inner sheet being at a lower density than the density of the outer sheet and interposed in the outer sheet, and absorbent polymers interposed between the fibers of the inner sheet, wherein the outer sheet is partially pressed while interposing the inner sheet, whereby the outer sheet is bonded to the inner sheet and the bonding parts thereof encircles a zone of a given area to arrange a plurality of encircled regions.

The inner sheet is a non-woven fabric formed from fibers of 2.0 denier or more to 10.0 denier or less and the inner sheet is preferably at a density of 0.01 g/cm$^3$ or more to 0.06 g/cm$^3$ or less.

The absorption core is preferably of such a structure that the inner sheet is overlaid on the inside of the outer sheet and absorbent polymers are placed between the fibers of the inner sheet and both the sides of the outer sheet in the width direction are folded, together with the inner sheet, to laminate both the sides of the outer sheet in such a manner that the outer sheet might wrap the inner sheet so that the outer sheet is partially bonded together while interposing the inner sheet in the outer sheet.

The absorption core is produced by a method comprising a step of overlaying the inner sheet over the inside of the outer sheet, a step of uniformly dispersing the absorbent polymers between the fibers of the inner sheet, a step of inwardly folding both the sides of the outer sheet, along with the inner sheet, to laminate together both the sides of the outer sheet so as to wrap the inner sheet, and a step of pressing together the outer sheet while interposing the inner sheet, thereafter hot melting or bonding the outer sheet with the inner sheet or hot melting or bonding the inner sheet together, by means of a hot melt adhesive.

The absorbent article in accordance with the present invention is used for protectors against incontinence, disposable diapers and sanitary napkins. The absorption core is bonded to for example a paper sheet preliminarily formed into a shape fitting to the body shape of a wearer, by means of hot melt adhesive, then an absorbent top sheet is bonded to the inside of the absorption core and a back sheet is bonded to the outside of the paper sheet, for example, which is then provided for use.

The inner sheet comprises a bulky, coarse air-through non-woven fabric. Then, absorbent polymers for example are placed on the inner sheet, which is folded from both the sides thereof to wrap the absorbent polymers, so that the absorbent polymers are interposed between the fibers of the inner sheet.

As the absorbent polymers, mainly, use is made of super absorbent polymers (SAP) with high absorptivity and water rententivity, such as polyacrylic acid salts. As the SAP, use is made of a variety of substances including synthetic polymers such as polyvinyl alcohols and polyacrylamides or starches and celluloses, other than the polyacrylic acid salts.

The SAP are interposed into the inner sheet, but because the inner sheet is an air-through non-woven fabric at a low density and with a great number of spaces between the fibers, the SAP can be retained in the spaces between the fibers of the inner sheet. When urine and blood of menstruation are spotted, then, the SAP swell in the spaces of the fibers. As has been described above, the inner sheet is so coarse and bulky that there are lots of spaces capable of allowing the swelling of the SAP. Therefore, the space for SAP to swell can be secured therein. Thus, the SAP can absorb urine and blood of menstruation so that the SAP can sufficiently swell and exert the absorptivity well. Accordingly, the absorptivity can be enhanced even at a smaller amount of the SAP, so that the resulting absorbent article can be prepared of a slim type.

So as to form a space capable of allowing the swelling of the SAP inside the inner sheet as described above, the inner sheet is a non-woven fabric formed of fibers of preferably 2.0 denier or more to 10.0 denier or less, more preferably 4.0 denier or more to 6.0 denier or less. Additionally, the density of the inner sheet is preferably 0.01 g/cm$^3$ or more to 0.06 g/cm$^3$ or less, more preferably 0.03 g/cm$^3$ or more to 0.05 g/cm$^3$ or less. The thickness of the inner sheet is 0.4 mm or more to 0.6 mm or less.

The outer sheet of a hydrophilic non-woven fabric is overlaid on the outside of the inner sheet. So as to elevate the bonding strength at the bonding parts, in particular, the outer sheet is preferably a point-bond non-woven fabric containing 100% of a hot melt fibers (thermoplastic fibers) Furthermore, preferably, the outer sheet is preliminarily processed with a hydrophilic surfactant. The outer sheet should be at a higher density than the density of the inner sheet so as to prevent the outward pouring of the absorbent polymers having been poured out from between the fibers of the inner sheet. Preferably, thus, the outer sheet is formed of fibers of 1.0 denier or more to 4.0 denier or less and with a base weight of 10 g/m$^2$ or more to 60 g/m$^2$ or less.

After overlaying the outer sheet over the inner sheet to wrap the absorbent polymers by the two types of the sheets, the outer sheet and the inner sheet are bonded together while the inner sheet is bonded together. More specifically, the outer sheet is bonded together under pressure at a state while the outer sheet interposes the inner sheet. When the inner sheet and the outer sheet made of hot melt resin such as polypropylene(PP) and polyethylene(PE) is/are mixed with the inner sheet and the outer sheet, the outer sheet is pressed and heated, to bond the outer sheet with the inner sheet and bond the inner sheet together, by hot melting the fibers together. The bonding parts by means of hot melting should be formed over the whole surface of an absorbent article (absorbent sheet), so that an encircled region of a hexagonal shape or an encircled region of a diamond shape can be formed by the bonding parts. The absorbent polymers such as SAP can shift only in a limited zone in the encircled region. Hence, the absorbent polymers can be dispersed uniformly in the absorbent sheet. Furthermore, SAP swell in the zone in the encircled region, and the area of the encircled region can be determined freely at the hot melting process. In accordance with the present invention, the area of the encircled region is 1.0 cm$^2$ or more to 10.0 cm$^2$ or less, whereby the space for SAP to swell can be secured. Even if SAP make shift in the encircled region, the SAP distribution does not fall in non-uniformity, so that SAP can be dispersed uniformly in the absorbent article.

Preferably, the bonding strength at the bonding parts is such a strength that the bonding parts can be peeled off when the absorbent polymers swell in the inner sheet after absorption of urine and blood of menstruation.

The absorbent article (absorbent sheet) of the present invention contains the absorbent polymers in the inner sheet, and absorbs urine and blood of menstruation mainly through the absorbent polymers, where urine and blood of menstruation are retained. As the absorbent polymers, therefore, use is made of absorbent polymers of a high absorption ratio (or with a greater absorption amount) and at a faster absorption rate, preferably. If the absorption rate is slow, urine and others are readily oozed out from the absorbent article. If the absorption ratio is low (the absorption amount is less), alternatively, urine and blood of menstruation absorbed therein are reduced.

When SAP with a larger absorption ratio and a faster absorption rate is used, the space for the SAP to swell should necessarily be secured in the inner sheet, at a state prior to absorption of urine or blood of menstruation. Preferably, therefore, the space ratio in the inner sheet is 40% or more to 60% or less. If the space ratio is smaller than the range described above, the space capable of allowing SAP to swell cannot sufficiently be secured. If the space ratio is above the range, SAP readily make shift in the inner sheet before absorbing urine and blood of menstruation, so that the SAP distribution therein turns non-uniform.

DETAILED DESCRIPTION OF THE PREFERRED EMBODIMENTS

Figure 1:
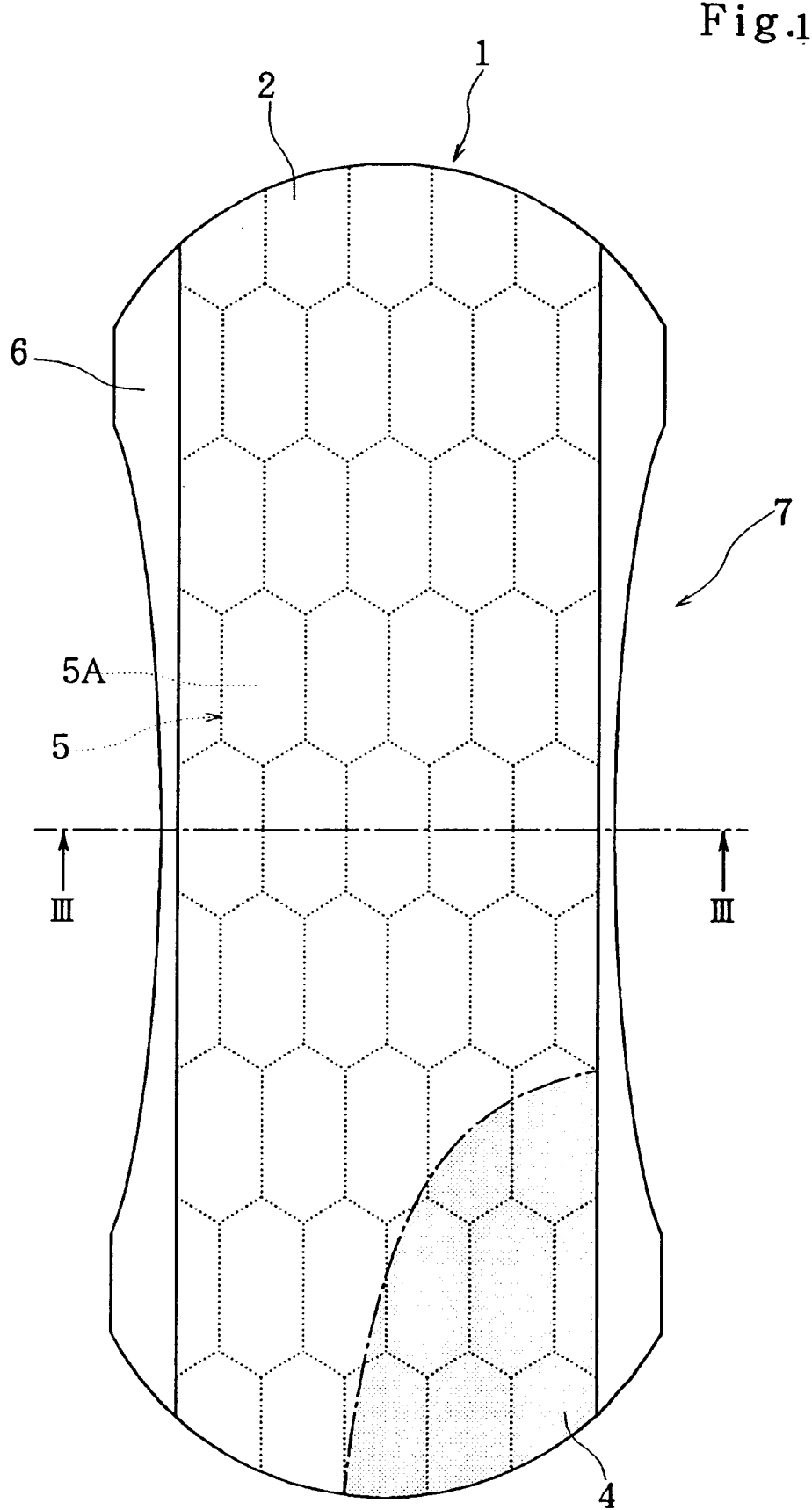
FIG. 1 is a plane view of the absorption core of the absorbent article in accordance with the present invention.
Figure 5:
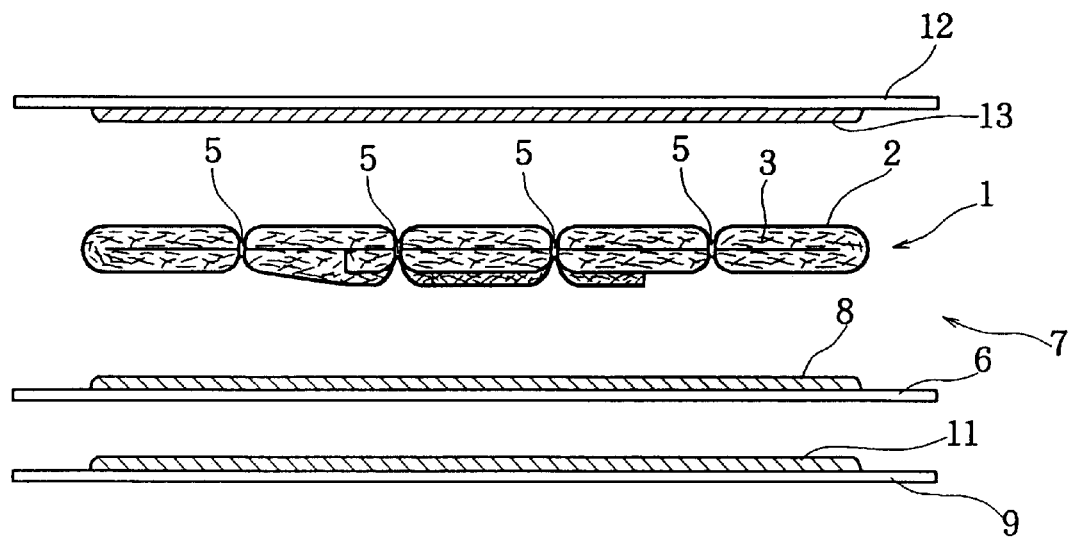
FIG. 5 is a cross sectional view depicting the absorption core of the present invention, the top sheet and the back sheet in separation.
Figure 6:
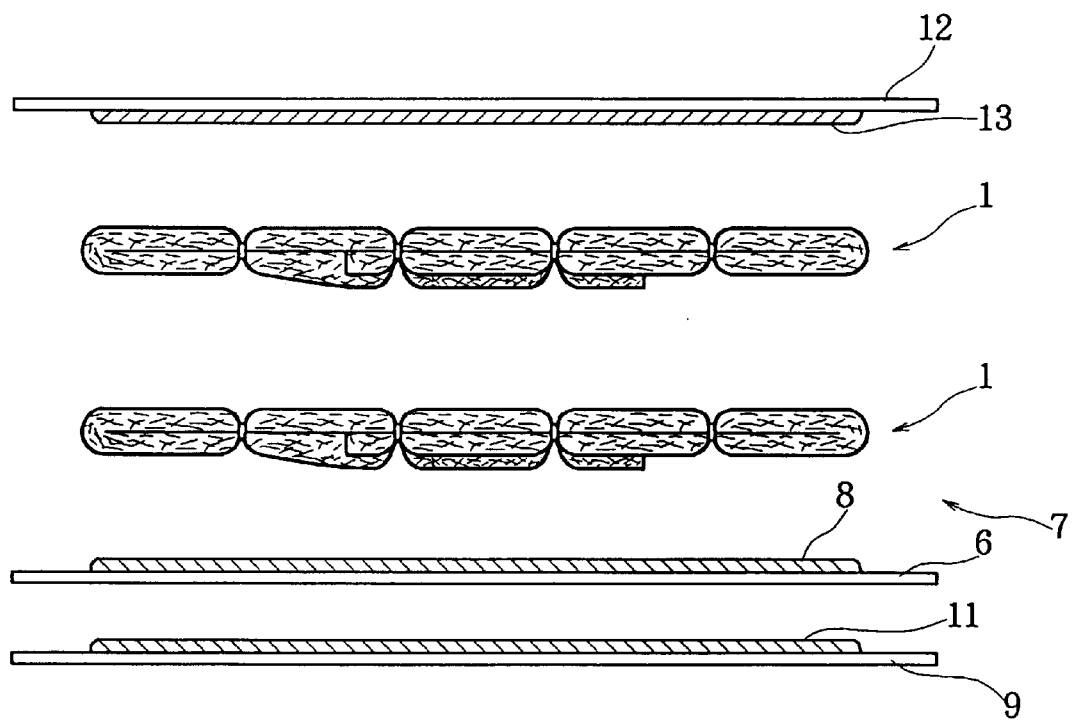
FIG. 6 is a cross sectional view depicting two absorption cores, the top sheet and the back sheet in separation.

As shown in FIG. 1, absorption core 1 formed in a rectangular shape is mounted on absorbent paper sheet 6 formed into a shape fitting to the body shape of a wearer and is then bonded to the paper sheet 6. The paper sheet 6 bonded to the absorption core 1 is used as absorbent sheet (absorbent article) 7 to be placed in protectors against incontinence, disposable diapers and sanitary napkins. When the absorbent sheet 7 is used for protectors against incontinence, disposable diapers and sanitary napkins, a top sheet and a back sheet are bonded to the upper side and lower side of the absorbent sheet 7, as shown in FIG. 5 or FIG. 6.

Figure 2:
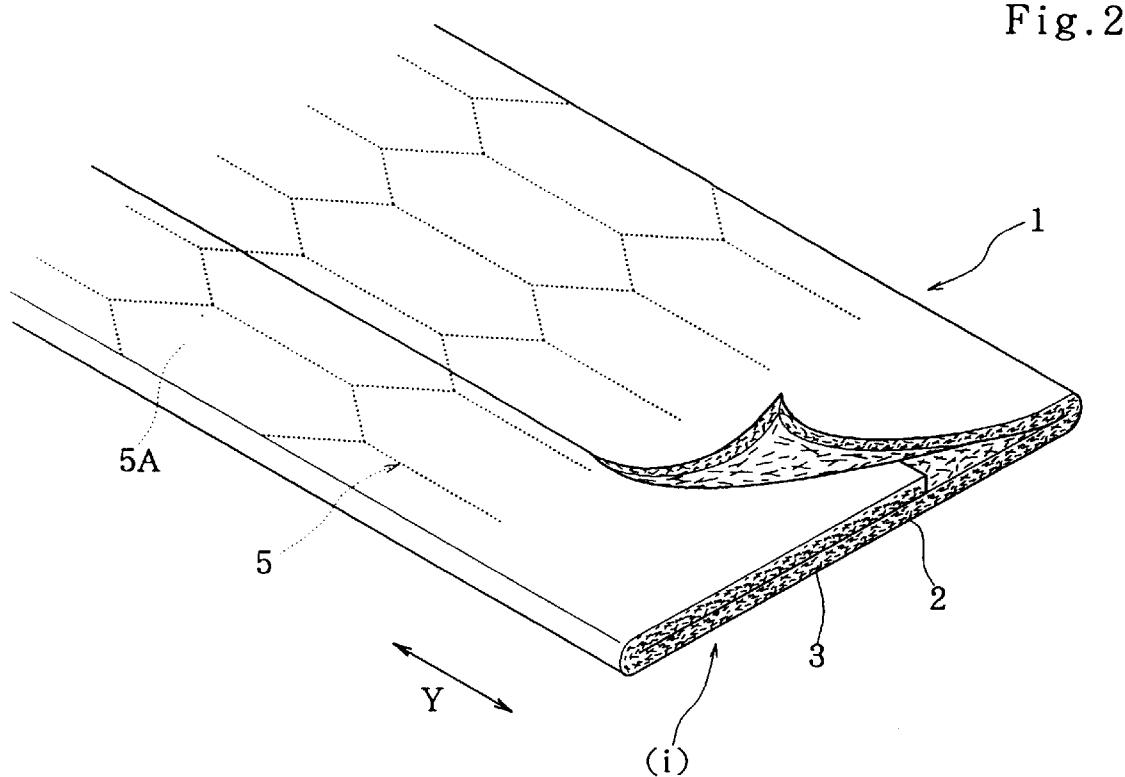
FIG. 2 is a perspective view of the absorption core.

In the absorbent core 1, as shown in FIG. 2, inner sheet 3 is overlaid on the inside of outer sheet 2. The inner sheet 3 is a bulky air-through non-woven fabric at a coarse density. The non-woven fabric is formed of complex fibers such as PE(polyethylene)/PP (polypropylene) or PE fiber or PP fiber or a combination of these fibers or fibers produced by coating a hydrophilic oil such as glycerin over the surface of these fibers or fibers produced by kneading the oil in these fibers or these fibers along with rayon fiber.

The air-through non-woven fabric to be used as the inner sheet 3 contains at least 20% or more of hot melt fibers. SAP 4 are interposed and retained between the fibers of the inner sheet 3. Because the space between the fibers is a space for SAP 4 to swell, the inner sheet 3 should be required to be coarse enough to allow the swelling of SAP 4. Therefore, the air-through non-woven fabric of the inner sheet 3 is formed of thick fibers of preferably 2.0 denier or more to 10.0 denier or less, more preferably 4.0 denier or more to 6.0 denier or less. Furthermore, the density of the inner sheet is preferably 0.01 g/cm$^3$ or more to 0.06 g/cm$^3$ or less, more preferably 0.03 g/cm$^3$ or more to 0.05 g/cm$^3$ or less. Additionally, the thickness is preferably about 0.4 mm to 0.6 mm.

The space ratio in the inner sheet 3 (non-woven fabric) is 40% or more to 60% or less.

The space ratio (%) described above is represented by the formula $[100-(M/T \cdot \rho)]$.

M (g/cm$^2$) is the base weight per 10 cm$^2$ of the inner sheet. T (mm) is the thickness of the inner sheet, which is determined by overlaying 10 sheets of the inner sheet together and applying a pressure of 20 gf/cm$^2$ to the overlaid sheets to measure the thickness of the 10 sheets and calculating the thickness of one sheet on the basis of the measured thickness. $\rho$ (g/cm$^3$) is the density of the inner sheet.

Figure 4:
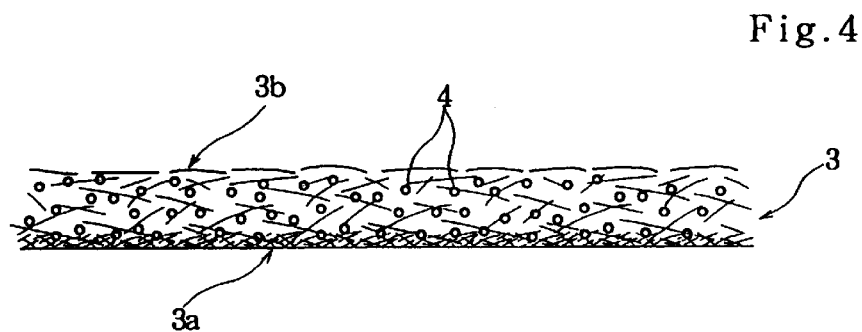
FIG. 4 is an enlarged cross sectional view of the inner sheet.

FIG. 4 is an enlarged cross sectional view of the inner sheet 3. As described above, the inner sheet 3 is a bulky air-through non-woven fabric at a coarse density. Because one face 3a of the air-through non-woven fabric is subjected to a heat roller, the side of the one face 3a is at a higher density, while the side of the other face 3b is at a lower density. Thus, the distance between the fibers is smaller than the particle diameter of SAP 4 on the side of one face 3a, so that the SAP 4 are hardly poured out from the face 3a. Alternatively, the side of the other face 3b is at a lower density so that sufficient space for SAP to swell can be formed between the fibers on the side of the other face 3b. Hence, the side of one face 3a is preferably directed toward the outer sheet 2 for use.

As has been described above, the inner sheet is so bulky at a coarse density, whereby the powder of SAP 4 at dry state can be contained in the space between the fibers. Furthermore, because the space between the fibers works as a space for SAP 4 to swell, the absorptivity of the SAP 4 can satisfactorily be exerted therein with no loss, and additionally, the absorption core 1 can be prepared of a slim type.

The outer sheet 2 has a higher density than the density of the inner sheet 3, in order that the super absorbent polymers (SAP) 4 poured out from the space between the fibers of the inner sheet 3 won't be poured outside. The outer sheet 2, liquid permeable, is formed of for example thin hot melt fibers of 1.0 denier or more to 4.0 denier or less, by using a point-bond non-woven fabric with a base weight of 10 g/m$^2$ or more to 60 g/m$^2$ or less. Additionally, the point-bond non-woven fabric contains at least 20%, preferably 100% of hot melt fibers such as PE fiber, PP fiber or PE/PP complex fiber.

More specifically, so as to bond the outer sheet 2 and the inner sheet 3 together or bond together the inner sheet 3 as being faced to itself, at least 20% of hot melt fibers such as PP fiber or PE fiber are preferably contained in the inner sheet 3 and the outer sheet 2. When these sheets contain 100% or nearly 100% of the hot melt fibers, these sheets can be hot melted and bonded together strongly at the bonding parts at a higher rate.

When the outer sheet 2 is a point-bond non-woven fabric formed from hot melt fibers, the density thereof is preferably 0.1 g/cm$^3$ or more to 0.15 g/cm$^3$ or less. If the density is above 0.15 g/cm$^3$, the urine or blood of menstruation hardly permeates through the inner sheet. If the density is below 0.1 g/cm$^3$, alternatively, the SAP in the inner sheet is readily poured outside the outer sheet.

As the super absorbent polymers (SAP) 4 to be retained between the fibers of the inner sheet 3, use is made of a variety of polymers, for example polyacrylate salts or synthetic polymers such as polyvinyl alcohols and polyacryl amides, or starches and celluloses.

When the absorption core 1 of the present invention is used as for example an absorption sheet for protectors against incontinence and the super absorbent polymers (SAP) are used therein as the absorbent polymers, the absorption core 1 absorbs artificial urine of 15 cc per 1 g of the super absorbent polymers where the urine is spotted, preferably within 7 seconds and more preferably within 4 seconds. If the absorption rate exceeds 10 seconds, urine is readily oozed out from the absorption core 1. Preferably, use is made of such a SAP that can absorb fluid of a volume of 50-fold or more to 60-fold or less the volume of the SAP at its dry state. As to the volume of urine absorbed into SAP, furthermore, SAP of 1 g at its dry state can absorb artificial urine of about 60 g or more to 70 g or less; as to the volume of fluid to be retained in SAP, preferably, SAP of 1 g at its dry state can retain artificial urine of about 35 g or more to 45 g or less.

The super absorbent polymers satisfying the conditions described above include for example polymers absorbing agent produced by suspending acrylic acid and an aqueous solution of an alkali salt of acrylic acid in a solvent of an alicyclic hydrocarbon in the presence of a surfactant of HLB 8 to 12 or in a solvent of an aliphatic hydrocarbon of HLB 8 to 12, and reversibly suspending and polymerizing the resulting suspension in the presence of a water-soluble radical initiator.

The surfactant of HLB 8 to 12 includes for example sorbitan monolaurate.

As the solvent of an alicyclic hydrocarbon, cyclopentane, methyl cyclopentane, cyclohexane, and methyl cyclohexane are appropriate. As the solvent of an aliphatic hydrocarbon, n-pentane, n-hexane, n-heptane and ligroin are appropriate.

As the radical initiator, potassium persulfate and ammonium persulfate are appropriate.

The bridging agent to be used for the polymerization appropriately includes water-soluble diglycidyl ether compounds [for example, poly(ethylene glycol diglycidyl ether), poly(propylene glycol diglycidyl ether)], haloepoxy compounds including for example epichlorohydrin and α-methyl epichlorohydrin, aldehyde compounds including for example glutaric aldehyde, glyoxal, and thiodiacetaldehyde.

As has been described above, preferably, SAP with an absorption rate of 7 seconds or less and an absorption ratio (volume of absorption) of 50-fold to 60-fold is placed on the inner sheet 3 with the space ratio of 40% to 60% or is interposed in the space in the inner sheet 3, so that the resulting base weight of the SAP charged in the inner sheet might be 100 g/m$^2$ or more to 150 g/m$^2$ or less and the resulting charged density of the SAP in the inner sheet might be 0.25 g/cm$^3$ or more to 0.45 g/cm$^3$ or less. By defining the base weight and density as such, the SAP can rapidly absorb urine and blood of menstruation in the space of the inner sheet 3, and therefore, sufficient volumes of urine and blood of menstruation can be absorbed into the absorbent article without any urine or blood of menstruation oozing outside.

As to the grain distribution of the SAP, the following permeability ratios are preferable for the inner sheets of the following meshes;

for 12 mesh; permeability ratio of 100% for 32 to 48 meshes; permeability ratio of 20% or more to 60% or less for 48 to 80 meshes; permeability ratio of 20% or more to 60% or less for 80 to 145 meshes; permeability ratio of 0% or more to 15% or less.

Figure 3A:
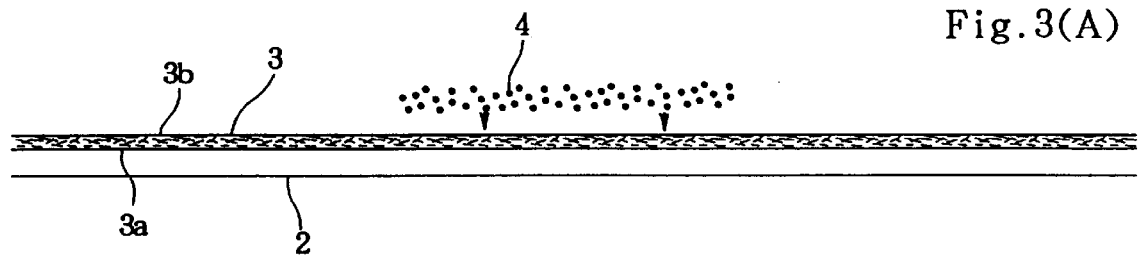
FIGS. 3 (A), (B) and (C) are cross sectional views of the absorption core of FIG. 1 along line III—III, sequentially depicting the process of producing the absorption core.
Figure 3B:
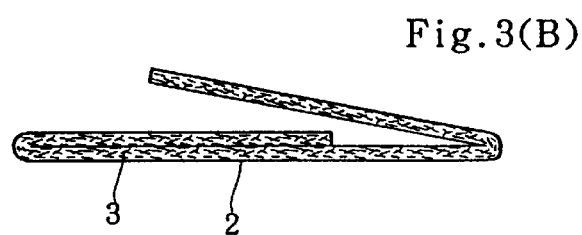

As shown in FIG. 3(A), the inner sheet 3 of the same width dimension and the same area as the outer sheet 2 is overlaid on the inside of the outer sheet 2. Then, over the inner sheet 3, SAP 4 are dispersed uniformly on the inner sheet 3. Subsequently, as shown in FIG. 3(B), both the sides of the outer sheet 2 in the width direction are folded along with the inner sheet 3, so both the sides of the outer sheet 2 and both the sides of the inner sheet 2 are overlaid together. In such manner, the inner sheet 3 and SAP 4 are wrapped by means of the outer sheet 2.

Figure 3C:
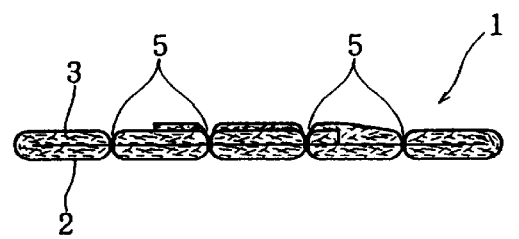

As shown in FIG. 3(C), subsequently, the laminated body of the outer sheet 2 and the inner sheet 3 is transferred to a heat roller, by which the laminated body is partially pressed and heated on protrusions formed on the roller, for thermally melting and bonding the outer sheet 2 and the inner sheet 3 together. In such fashion, bonding parts are formed. As shown in FIG. 1 and FIG. 2, the bonding parts 5 are in the form of continuous lines or uncontinuous lines. The lines of the bonding parts makes/make a pattern of hexagonal shape, to draw carapace-like patterns. In FIG. 3(C), the laminated body is pressed and melted so that the outer sheet 2 might be depressed from both the surface and back thereof at the bonding parts 5, but the outer sheet 2 is satisfactorily depressed on the bonding parts 5 from only a single face of the surface or back thereof.

In the absorption core 1 thus produced, the outer sheet 2 and the inner sheet 3 are folded at both the sides thereof in the width direction, as shown in FIG. 3(C). Therefore, the absorption core 1 in its entirety is covered with the outer sheet 2, and inside the outer sheet 2, SAP 4 are interposed with the inner sheet 3. Because the absorption core 1 is at such a state that SAP 4 are interposed with the inner sheet 3 and the inner sheet 3 is wrapped inside the outer sheet 2, SAP 4 are hardly poured out outside the absorption core 1. Because the inner sheet 3 is overlaid in two layers inside the outer sheet 2, furthermore, the volume of the space to retain SAP 4 can be enlarged inside the outer sheet 2, so that the zone capable of allowing the swelling of SAP4 can be secured as a large area.

SAP 4 wrapped in the inner sheet 3 cannot totally absorb urine or blood of menstruation if the volume is less. If the volume is too much, alternatively, swelling SAP 4 cannot sufficiently be retained in the space between the fibers of the inner sheet 3, which prevents the swelling of SAP 4. Hence, SAP 4 have a base weight of preferably 10.0 g/m$^2$ or more to 500 g/m$^2$ or less, more preferably 100 g/m$^2$ or more to 150 g/m$^2$ or less. If the absorption rate thereof is too slow, SAP 4 cannot sufficiently absorb urine or blood of menstruation if it is spotted continuously. Then, urine or blood of menstruation may be oozed out sideward. Therefore, the satisfactory absorption rate of SAP 4 is as follows; when the absorption rate is measured by a vortex method comprising placing 2.0 g of SAP 4 in 50 ml of an aqueous 0.9% solution of sodium chloride at 25° C. and counting the time until the vortex generated on the surface of the aqueous solution by the charging of SAP 4 disappears (the time when SAP absorb the aqueous solution and swells sufficiently), the time counted should be at least 10 seconds or less, preferably 7 seconds or less and more preferably 4 seconds or less.

As shown in FIG. 1, the shape of encircled region 5A, encircled with the bonding parts 5 where the outer sheet 2 and the inner sheet 3 are melted and bonded together and the inner sheet 3 of itself is also melted and bonded together, is a hexagonal shape (or a diamond shape, satisfactorily). Because the shift of SAP4 at its dry state is limited to the inside of the encircled region 5A, the distribution of SAP 4 does not fall into non-uniformity. Thus, SAP 4 can be dispersed uniformly inside the absorption core 1. Therefore, SAP 4 can be present on a portion to be spotted with urine or blood of menstruation with no exception, so that urine or blood of menstruation can be absorbed effectively into SAP 4. If the area of the encircled region 5A is small, however, the area of the bonding parts 5 is relatively large, which causes the reduction of the volume of the inner sheet. Accordingly, the space fixing SAP 4 and allowing the swelling thereof is reduced inside the inner sheet 3, unpreferably. If the area of the encircled region 5A is large, alternatively, SAP 4 make shift in the encircled region 5A, which causes non-uniform distribution of SAP 4, disadvantageously. Therefore, the area of each encircled region 5A is 1.0 cm$^2$ or more to 10.0 cm$^2$ or less, preferably about 3.0 cm. When the base weight of SAP 4 in the inner sheet is 130 g/m$^2$ and the area of one encircled region 5A is 3.0 cm$^2$, for example, the amount of SAP 4 present in one encircled region 5A is 0.042 g.

In the absorption core 1 shown in FIG. 1 and FIG. 2, the bonding parts in zigzag lines extends toward both the directions of the absorption core 1, namely the width direction and length direction thereof. The bonding parts 5 are in continuous lines or uncontinuous lines where the melted part and non-melted part are alternately aligned. A part of urine or blood of menstruation flowing onto the surface of the outer sheet 2 immediately permeates through the outer sheet 2 into the inner sheet 3. However, apart of urine or blood of menstruation flows along the bonding parts extending in zigzag lines and is subsequently dispersed toward the length direction and width direction of the absorption core 1. When the bonding parts 5 is in zigzag lines, the flow of urine or blood of menstruation gets longer. Therefore, urine or blood of menstruation readily permeates through the outer sheet 2 to infiltrate into the inner sheet 3, during the flow of urine or blood of menstruation along the bonding parts 5. When the bonding parts 5 are in uncontinuous lines, additionally, the flow rate of urine or blood of menstruation flowing along the bonding parts 5 is reduced, so that urine or blood of menstruation more readily permeates through the outer sheet 2 to infiltrate into the inner sheet 3. Hence, the outward oozing of urine or blood of menstruation can be prevented.

In FIG. 1, the bonding parts 5 are in zigzag lines, but the bonding parts may satisfactorily be in curved lines or lines mixed with curved lines and zigzag lines. Depending on the article in which the absorption core 1 is used, the lines formed by the bonding parts 5 may vary, for example continuous lines or uncontinuous lines.

In the absorption core 1, then, absorbent polymers are dispersed inside the encircled region 5A, around the bonding parts 5, and between the bonding parts 5 when the bonding parts 5 are formed uncontinuously. When urine or blood of menstruation is spotted on the absorption core 1, the absorbent polymers absorb urine or blood of menstruation and then swells consequently. When the region inside the inner sheet is finely divided by the encircled regions 5A, the space capable of allowing the swelling of the absorbent polymers cannot be sufficiently secured. Therefore, the individual bonding parts of the inner sheet are preferably peeled off, following the increase of the volume of absorbent polymers of an absorption ratio (amount of absorption) of 50-fold or more, when the polymers absorb urine or blood of menstruation and consequently swells.

When the bonding strength of the bonding parts 5 is set nearly at such a degree, the absorbent polymers are divided by each encircled regions prior to absorption of urine or blood of menstruation, so that the polymers are dispersed at a uniform density in the sheet. When urine or blood of menstruation is rapidly absorbed therein, then, the bonding parts of the inner sheet are peeled off so that the space allowing the swelling of SAP in the inner sheet can be secured.

Provided that the space ratio in the inner sheet is within the range and the absorbent polymers with a higher absorption ratio (amount of absorption) are placed on the inner sheet or are interposed in the space of the inner sheet to the final base weight and density as described above, the bonding strength of the inner sheet is approximately such a strength that a bonding part of a 25-mm width can be peeled off at a power of 20 gf or more to 50 gf or less.

If the melt strength of the bonding parts 5 is weak in those articles for use, such as sanitary napkins and disposable diapers for night use, the swelling SAP 4 shift in the absorption sheet to give unpleasant feeling to a wearer or the mass of the swelling SAP 4 tears or breaks the inner sheet 3 and the outer sheet 2. In such case, therefore, the melt strength of the bonding parts 5 should be elevated preferably, to securely retain the swelling SAP 4 in the encircled region 5A.

The thickness, rigidity and softness and the like of the absorption core 1 vary, depending on the materials of the outer sheet 2 and the inner sheet 3. So as to avoid the occurrence of unpleasant feeling in a wearer and have satisfactory absorptivity to the absorption core, preferably, the thickness thereof is 1.0 mm or more to 5.0 mm or less, preferably 1.0 mm or more to 2.5 mm or less; the rigidity and softness thereof in the CD direction (cross direction) as measured by taper method is 4 g·cm/25 mm or more to 30 g·cm/25 mm or less, preferably 4 g·cm/25 mm or more to 10 g·cm/25 mm or less.

The absorption core 1 thus formed extends in the Y direction as shown in FIG. 2, and then, the absorption core 1 is cut in a given size along the Y direction, which is subjected for use. The cut face (i) is sealed by thermally melting the outer sheet 2 and the inner sheet 3 or bonding these sheets together by means of an adhesive. Then, placing the absorption core 1 on absorbent paper sheet 6 formed so as to fit the crotch part of a wearer and coating partially hot melt adhesive 8 on the paper sheet 6 and the outer sheet 2 on their facing area thereby bonding the paper sheet 6 and the outer sheet 2 together, absorbent sheet 7 is prepared. Then, the length of the absorption core 1 in the width direction is almost the same length as the length of the paper sheet 6 in the width direction.

As shown in FIG. 5, in the absorbent sheet 7, the absorption core 1 is bonded to the paper sheet 6 by means of the adhesive 8 in such a manner that the area where both the sides of the laminated body of the inner sheet 3 overlaid on the outer sheet 2 are overlaid together might be toward the opposite side to the side to be spotted with urine or blood of menstruation. Then, the face on the opposite side to the face where both the sides of the sheets are overlaid together is toward the side to be spotted with urine or blood of menstruation, and to that face is partially bonded top sheet 12 facing the skin side of a wearer by means of hot melt adhesive 13. Then, back sheet 9 is bonded to the paper sheet 6 by means of hot melt adhesive 11.

As shown in FIG. 6, furthermore, two sheets of absorption core 1 are satisfactorily bonded and fixed on the paper sheet 6.

In the aforementioned embodiments, the inner sheet and the outer sheet are folded to wrap SAP from the top and bottom thereof. However, the present invention is not limited to these embodiments; for example, SAP are interposed between two sheets of the inner sheet and then, the outer sheets are overlaid on the outside of the two inner sheets, to melt and bond the end parts of the inner sheets and the outer sheets to seal SAP therein. So as to prevent the outward pouring of SAP, then, a sheet of a higher density than the density of the outer sheet facing the side of the top sheet may satisfactorily be used, as the outer sheet facing the side of the back sheet.

As has been described above, in the absorbent article of the present invention, the absorbent polymers can swell in the space between the fibers of the inner sheet of a coarse density and high bulkiness. Because encircled regions are formed by the bonding parts of bonding the outer sheet with the inner sheet or the bonding parts of bonding the inner sheet together and the shift of the absorbent polymers can be prevented in the encircled regions, the absorbent polymers can be dispersed uniformly in the absorbent article. Hence, an absorbent article of high absorptivity and a slim type can be produced.

When the bonding parts are in curved lines or in zigzag lines, extending in the width direction or/and length direction of the absorbent article and when urine or blood of menstruation is dispersed along the lines of the bonding parts, the dispersion of urine or blood of menstruation can be prevented due to the presence of the curved lines or zigzag lines. Therefore, urine or blood of menstruation does not flow out in the width direction or length direction of the absorbent article, and thus, the absorbent article can absorb urine or blood of menstruation, through the absorbent polymers.

If the bonding parts include an uncontinuous part, the dispersion of urine or blood of menstruation can be stopped at the uncontinuous part, and therefore, the absorbent polymers can absorb urine or blood of menstruation, more effectively, whereby the outward oozing of urine or blood of menstruation can be prevented.

If the absorbent polymers are wrapped with the outer sheet and the inner sheet at both the sides of the absorbent article, the absorbent polymers are not poured outside. Thus, the production of such absorbent article can be done more readily.

What is claimed is:

1. An absorbent article comprising a liquid non-permeable back sheet, a liquid permeable top sheet and an absorption core interposed between the back sheet and the top sheet, wherein the absorption core comprises at least one each of an outer sheet having a high density and a bulky inner sheet having a lower density than the density of the outer sheet, and absorbent polymers charged in between fibers of the inner sheet, wherein the outer sheet and the inner sheet are partially bonded together with the inner sheet surrounded the outer sheet, and wherein a plurality of regions of a given area are surrounded by at least one bonding part of the partially bonded together outer sheet and inner sheet.

2. An absorbent article according to claim 1, wherein the inner sheet is a non-woven fabric at a density of 0.01 g/cm$^3$ or more to 0.06 g/cm$^3$ or less and the outer sheet is a non-woven fabric at a density of 0.1 g/cm$^3$ or more to 0.15 g/cm$^3$ or less.

3. An absorbent article according to claim 1, wherein the area of the regions surrounded by said at least one bonding part is 1.0 cm$^2$ or more to 10.00 cm$^2$ or less.

4. An absorbent article according to claim 1, wherein the absorbent polymers can absorb urine or blood of menstruation at a volume 50-fold or more the volume of the absorbent polymers at its dry state and the charged density of the absorbent polymers is 0.25 g/cm$^3$ or more to 0.45 g/cm$^3$ or less.

5. An absorbent article according to claim 1, wherein the at least one bonding part is in continuous lines with curved parts.

6. An absorbent article according to claim 5, wherein the outer sheet and the inner sheet contain thermoplastic fibers and the thermoplastic fibers contained in the outer sheet and the inner sheet are thermally melted and bonded together at the bonding part, whereby the outer sheet and the inner sheet are bonded together or the inner sheet is bonded together.

7. An absorbent article according to claim 6, wherein the bonding strength of the at least one bonding part is a strength at such a degree that the at least one bonding part is broken when the absorbent polymers absorb urine or blood of menstruation and then swell in the space between the fibers of the inner sheet.

8. An absorbent article according to claim 1, wherein the at least one bonding part is in uncontinuous lines with curved parts.

9. An absorbent article comprising a liquid non-permeable back sheet, a liquid permeable top sheet and an absorption core interposed between the back sheet and the top sheet, wherein the absorption core comprises an outer sheet at a high density, a bulky inner sheet having a lower density than the density of the outer sheet and overlaid on the outer sheet, and absorbent polymers charged in between the fibers of the inner sheet, wherein:

both sides of a laminated body of the inner sheet and the outer sheet are folded so that the inner sheet is on an inside and the outer sheet is on an outside, to overlay sides of the outer sheet together, the inner sheet and outer sheet are partially bonded together, and a plurality of regions of a given area are surrounded by at least one bonding part of the partially bonded together outer sheet and inner sheet.

10. An absorbent article according to claim 9, wherein the inner sheet and the outer sheet are bonded and sealed together at each end of the laminated body in a length direction.

11. An absorbent article according to claim 9, wherein the inner sheet is a non-woven fabric at a density of 0.01 g/cm$^3$ or more to 0.06 g/cm$^3$ or less and the outer sheet is a non-woven fabric at a density of 0.1 g/cm$^3$ or more to 0.15 g/cm$^3$ or less.

12. An absorbent article according to claim 9, wherein the area of each region surrounded by said at least one bonding part is 1.0 cm$^2$ or more to 10.0 cm$^2$ or less.

13. An absorbent article according to claim 9, wherein the absorbent polymers can absorb urine or blood of menstruation at a volume 50-fold or more the volume of the absorbent polymers at its dry state and the charged density of the absorbent polymers is 0.25 g/cm$^3$ or more to 0.45 g/cm$^3$ or less.

14. An absorbent article according to claim 9, wherein the at least one bonding part is in continuous lines with a curved part.

15. An absorbent article according to claim 14, wherein the outer sheet and the inner sheet contain thermoplastic fibers and the thermoplastic fibers contained in the outer sheet and the inner sheet are thermally melted and bonded together at the bonding parts, whereby the outer sheet and the inner sheet are bonded together or the inner sheet is bonded together.

16. An absorbent article according to claim 15, wherein the bonding strength of the at least one bonding part is a strength at such a degree that the at least one bonding part is broken when the absorbent polymers absorb urine or blood of menstruation and then swells in the space between the fibers of the inner sheet.

17. An absorbent article according to claim 9, wherein the both sides of the laminated body are overlaid together at a back side and an opposite side is a top sheet of the laminated body.

18. An absorbent article according to claim 9, wherein the outer sheet and the inner sheet contain thermoplastic fibers and the thermoplastic fibers contained in the outer sheet and the inner sheet are thermally melted and bonded together at the at least one bonding part.

19. An absorbent article according to claim 9, wherein the thermoplastic fibers contained in the inner sheet are thermally melted at a surface of the inner sheet in contact to the outer sheet.

20. An absorbent article according to claim 9, wherein the at least one bonding part is in uncontinuous lines with curved parts.

* * * * *